United States Patent
Nelson

(10) Patent No.: US 7,101,390 B2
(45) Date of Patent: Sep. 5, 2006

(54) STAGED DEPLOYMENT ENDOGRAFT

(75) Inventor: Kristoff Nelson, Boston, MA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 10/445,406

(22) Filed: May 27, 2003

(65) Prior Publication Data

US 2004/0243215 A1    Dec. 2, 2004

(51) Int. Cl.
    *A61F 2/06*    (2006.01)
(52) U.S. Cl. .................... 623/1.12; 623/1.13
(58) Field of Classification Search ....... 623/1.11–1.35
    See application file for complete search history.

(56) References Cited

U.S. PATENT DOCUMENTS

| | | | |
|---|---|---|---|
| 5,405,378 A * | 4/1995 | Strecker | 623/1.12 |
| 5,871,536 A | 2/1999 | Lazarus | |
| 5,948,017 A | 9/1999 | Taheri | |
| 6,165,210 A * | 12/2000 | Lau et al. | 623/1.12 |
| 6,193,745 B1 | 2/2001 | Fogarty et al. | |
| 6,261,316 B1 * | 7/2001 | Shaolian et al. | 623/1.11 |
| 6,287,330 B1 | 9/2001 | Johansson et al. | |
| 6,352,561 B1 * | 3/2002 | Leopold et al. | 623/1.23 |
| 6,364,901 B1 | 4/2002 | Inoue | |
| 6,464,719 B1 | 10/2002 | Jayaraman | |
| 6,551,350 B1 | 4/2003 | Thornton et al. | |
| 2002/0099431 A1 | 7/2002 | Armstrong et al. | |
| 2002/0177890 A1 * | 11/2002 | Lenker | 623/1.12 |
| 2004/0019373 A1 * | 1/2004 | Casey et al. | 623/1.13 |
| 2004/0093063 A1 * | 5/2004 | Wright et al. | 623/1.12 |
| 2004/0106978 A1 * | 6/2004 | Greenberg et al. | 623/1.13 |

* cited by examiner

*Primary Examiner*—Suzette J-J Gherbi
(74) *Attorney, Agent, or Firm*—RatnerPrestia

(57) ABSTRACT

An apparatus is provided for deploying an endograft that maintains a fluid channel throughout deployment. A method for deploying an endograft maintaining a fluid channel through the deployment is also provided.

14 Claims, 5 Drawing Sheets

STAGED DEPLOYMENT ENDOGRAFT

FIELD OF THE INVENTION

The present invention is generally related to endoluminal grafts and more particularly related to an endoluminal graft that is deployable in stages.

BACKGROUND OF THE INVENTION

Endoluminal grafts, or endografts, are tubular grafts, widely used to repair body lumens, which are introduced to a lumen site in need of repair endoluminally from a distal lumen location. One application for such endografts is to exclude aneurysms in various body lumens. For procedural success, it is important to deploy the endograft such that its proximal and distal ends are fixed to relatively healthy tissue. It is also important to deploy the endograft such that it does not interfere with branch lumens or extend beyond the repair area. Thus, precise placement in the lumen is important. It is also desirable to maintain a flow of fluid during delivery and deployment of the endograft. Repair of aneurysms in high-pressure lumens, such as the thoracic aorta, is complicated by the force of fluid pressure acting on the endograft during deployment. This force makes it difficult to accurately place the endograft. Typically, the expansion of the endograft from a compressed configuration (in which it is delivered to the repair site) to its expanded deployed configuration is not instantaneous, but occurs longitudinally from one end of the graft to the other. As this occurs, fluid flow within the lumen causes a windsock effect, which applies longitudinal force to the endograft. This problem is exacerbated because typical endografts cannot be repositioned after deployment. It is believed that an endograft less susceptible to this problem would be useful.

SUMMARY OF THE INVENTION

The present invention comprises an endograft with a plurality of separately expandable longitudinal portions. In one embodiment, the invention comprises a self-expanding stent scaffold, a covering affixed to the stent scaffold, and one or more releasable restraining members configured to constrain (i.e., resist expansion of) associated longitudinal portions of the stent scaffold along its length. The restraining members provide a flow channel to maintain fluid flow external the endograft and proximate the restraining members during deployment while allowing remaining portions of the stent scaffold to expand.

BRIEF DESCRIPTION OF THE DRAWINGS

The invention is best understood from the following detailed description when read in connection with the accompanying drawings. It is emphasized that, according to common practice, the various features of the drawings are not to scale. On the contrary, the dimensions of the various features may be expanded or reduced for clarity. Included in the drawings are the following figures.

DETAILED DESCRIPTION OF THE INVENTION

Figure 6:
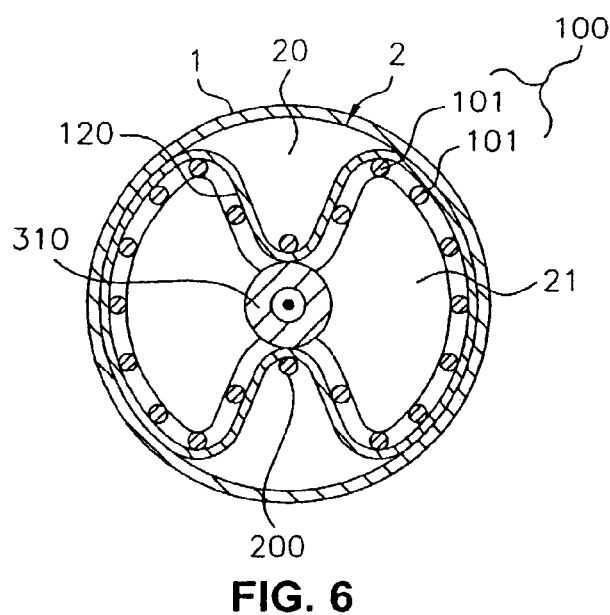
FIG. 6 is a cross-sectional view of the endograft and delivery system of FIG. 5 at plane 6–6' shown in FIG. 5.
Figure 7:
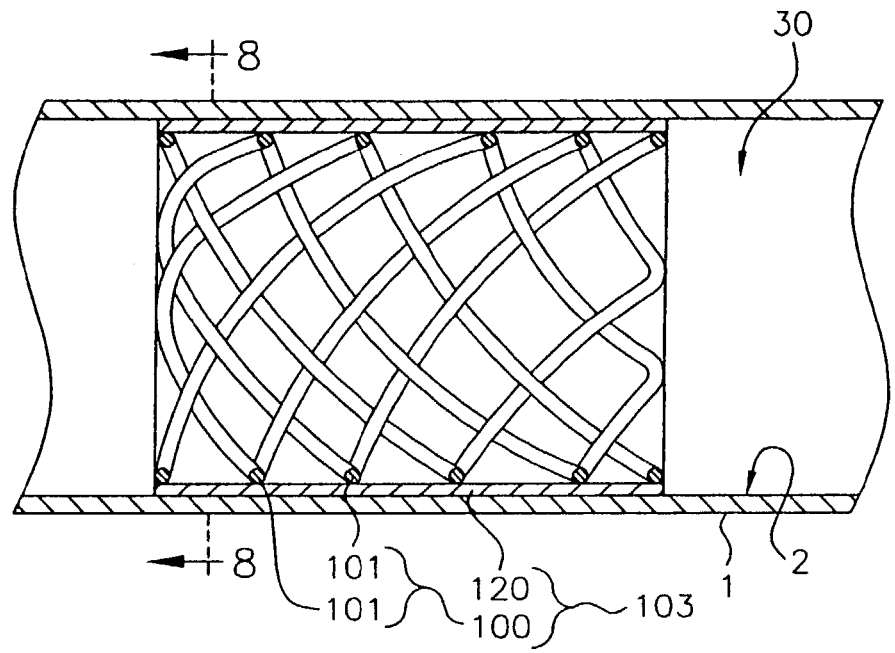
FIG. 7 is a subsequent sequential sectioned side view of the endograft of FIGS. 1, 3, and 5 in a fully deployed configuration within a body lumen following removal of the restraining members and delivery system according to an exemplary embodiment of the present invention.
Figure 8:
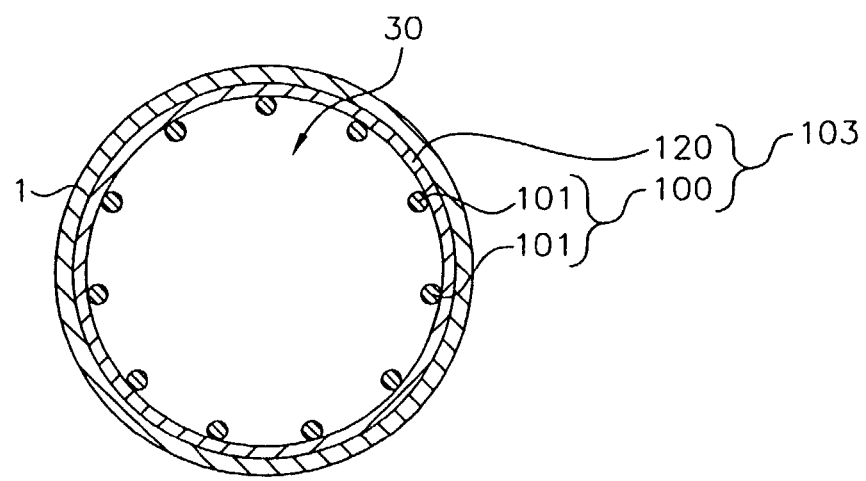
FIG. 8 is a cross-sectional view of the endograft of FIG. 7 at plane 8–8' in FIG. 7.

Referring now to the drawings, in which like reference numbers refer to like elements throughout, there is shown in FIGS. 1–8 an endograft 103 according to an exemplary embodiment of the present invention. As shown in FIG. 8, endograft 103 comprises a stent scaffold 100 with a covering 120 attached to stent scaffold 100. Covering 120 may be woven, knitted, expanded polytetrafluoroethylene (ePTFE) or any combination thereof. Covering 120 may be attached to stent scaffold 100 by sutures, adhesive, rings, staples, or other connective elements. Stent scaffold 100 comprises woven stent members 101 that are wound in opposing helical directions. Stent members 101 may comprise a shape memory material, such as nitinol making stent scaffold 100 self-expanding. Alternative self-expanding stent scaffold configurations (such as zig-zag stents, laser cut tubes, woven structures and the like), as well as balloon-expandable endograft configurations are contemplated within the scope of the present invention.

As shown in FIGS. 1 through 6, restraining members 200 extend longitudinally along stent scaffold 100 at diametrically opposed lines along the length of endograft 103. These restraining members 200 are operatively associated with selected longitudinal portions of endograft 103, such that they constrain (i.e., resist expansion of) the associated portions of endograft 103. In the exemplary embodiment shown in FIGS. 1 through 8, restraining members 200 are wires entwined in stent scaffold 100. Restraining members 200 may alternatively extend over longitudinal portions of endograft 103 to constrain underlying portions of the endograft. As described hereafter, the restraining members alternatively may be tubes, sutures, or other structures suitable for constraining the associated lengthwise portions of stent scaffold 100. In this embodiment, two restraining members are provided, to maintain stability of the endograft. Embodiments comprising one, three, four, or more restraining members are also contemplated within the scope of the invention.

Figure 1:
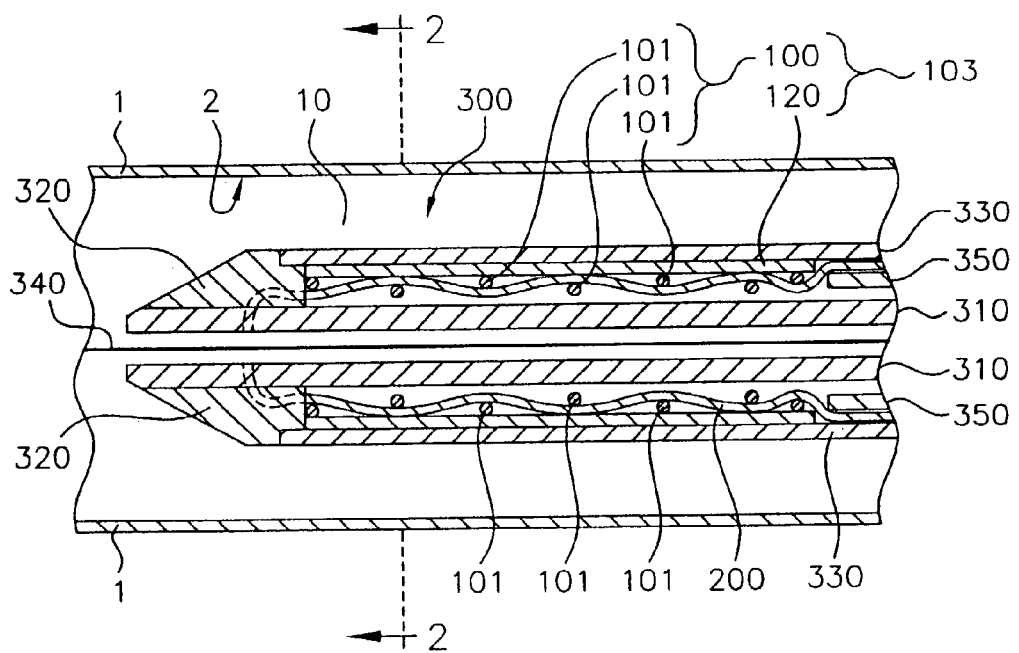
FIG. 1 is a sectioned side view of an endograft having a stent scaffold, compressed for endoluminal delivery, loaded in a delivery system with restraining members entwined through the stent scaffold, and positioned within a body lumen according to an exemplary embodiment of the present invention.

When endograft 103 is in its pre-deployed configuration (i.e., compressed for endoluminal delivery), as shown in FIG. 1, restraining members 200 are releasable, meaning that they can be manipulated such that they cease to constrain stent scaffold 100. Prior to release, restraining members 200 selectively constrain stent scaffold 100, preventing the selectively constrained portions of stent scaffold 100 from expanding to a fully expanded configuration. This constraint is selective in that portions of endograft 103 not in direct contact with releasable restraining members 200 are not constrained by releasable restraining members 200 allowing those portions of endograft 103 to expand. Following release, restraining members 200 are removed from endograft 103 (as shown in FIGS. 7 and 8).

Figure 2:
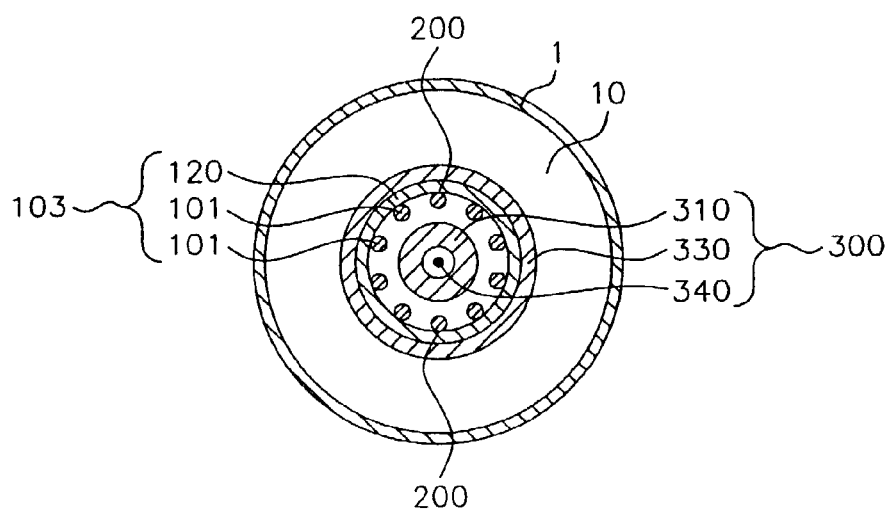
FIG. 2 is a cross-sectional view of the endograft and delivery system of FIG. 1 at plane 2–2' shown in FIG. 1.

As shown in FIGS. 1 and 2, endograft 103, together with releasable restraining members 200, is loaded in a delivery system 300 in its compressed configuration ready for delivery endoluminally into a body lumen 1. Delivery system 300 is sized to provide a fluid channel 10 between the loaded delivery system and the inner surface 2 of the body lumen 1 during endoluminal advancement of the delivery system. This fluid channel allows the endograft to be delivered without interrupting fluid flow in the body lumen.

Delivery system 300, as shown in FIGS. 1 through 6, comprises a catheter 310 for carrying endograft 103. Catheter 310 is generally tubular in shape, having a longitudinal aperture for receiving a guide wire 340. Catheter 310 is attached at its proximal end (i.e., the end first entering the body) to a nosecone 320, which is tapered to assist in advancing delivery system 300 through body lumen 1. A sheath 330 surrounds catheter 310 creating a cavity with an elongated torus shape for receiving endograft 103. Sheath 330 is configured to be axially movable relative to catheter 310, and more particularly to slide distally over endograft 103 carried on catheter 310, when sheath 330 is withdrawn from the endograft. A stabilizer 350 (sometimes referred to as a pusher) surrounds catheter 310 distally of endograft 103 for pushing or holding endograft 103 while sheath 330 is axially withdrawn or moved distally relative to the endograft.

As shown in FIGS. 1 and 2, sheath 330 constrains stent scaffold 100 (and covering 120 attached to scaffold 100) in a collapsed or compressed configuration in which its diameter is smaller than the body lumen to be repaired. Restraining members 200 are associated with lengthwise or longitudinal portions of stent scaffold 100 as described above, and attached at their proximal end to nosecone 320. At their distal end, restraining members 200 may extend inside sheath 330 to a control handle (not shown) which remains external the body. Tension is applied to restraining members 200 to provide the necessary restraining force to endograft 103. As shown in FIG. 1, diametrically opposed restraining members 200 may be joined and pass or loop through an aperture in nosecone 320, with both ends extending back to the handle (not shown). Tension is applied to restraining members 200 at the handle. In this configuration, restraining members 200 are released by releasing one end of the joined restraining members at the handle and removing the restraining members by pulling the other end of the joined restraining members back through the handle until the released end traverses the entire length of the delivery catheter 310 to nosecone 320 and back to the handle.

Alternatively, each restraining member 200 may be secured in nosecone 320 with a bio-absorbable or dissolvable adhesive, such that restraining members 200 are released when the adhesive is absorbed or dissolved. In yet another alternative embodiment, joined restraining members may loop through catheter 310 proximal to endograft 103 with both ends extending distally to the handle.

Restraining members 200 may alternatively extend between the stabilizer 350 and catheter 310, then through a hypotube (not shown), which connects to stabilizer 350, and catheter 310. In an alternative configuration, catheter 310 may comprise a second and third longitudinal aperture (not shown), and restraining members 200 may extend through these apertures.

Figure 3:
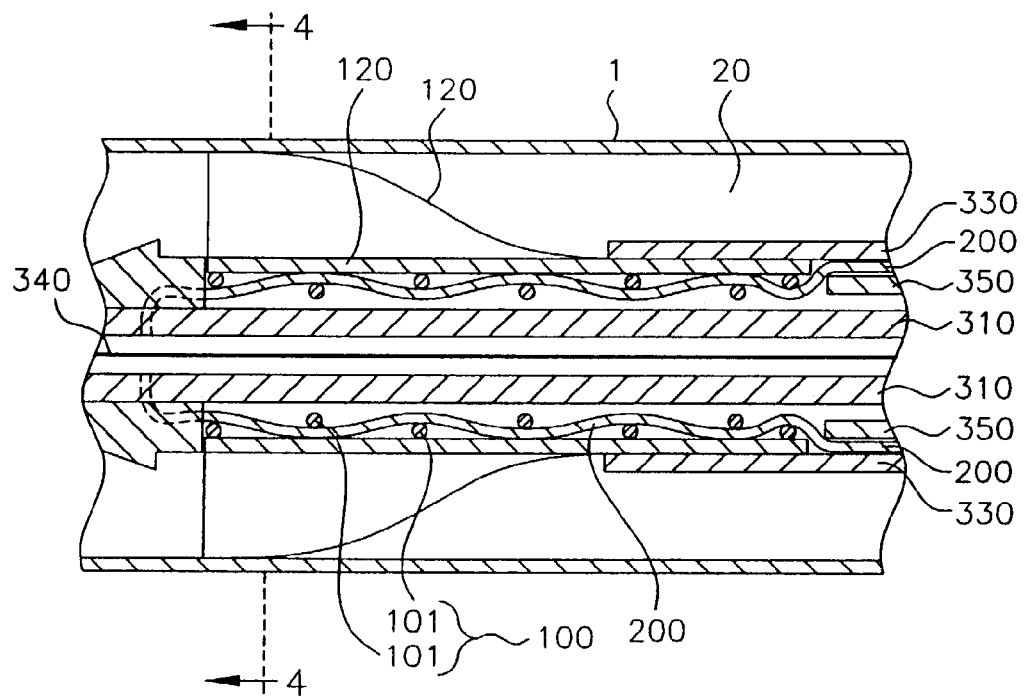
FIG. 3 is a subsequent sequential sectioned side view of the endograft and delivery system of FIG. 1 with the endograft at a first partially deployed stage according to an exemplary embodiment of the present invention.
Figure 4:
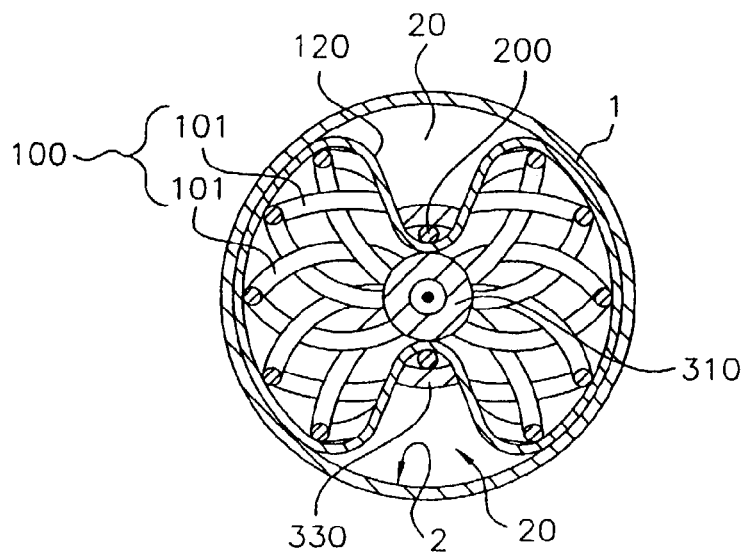
FIG. 4 is a cross-sectional view of the endograft and delivery system of FIG. 3 at plane 4–4' shown in FIG. 3.

As shown in FIGS. 3 and 4, when endograft 103 is advanced to its desired location in body lumen 1, it is partially deployed to a first deployed stage by withdrawing sheath 330 from endograft 103. As sheath 330 is partially withdrawn, restraining members 200 constrain associated lengthwise portions of stent scaffold 100, while circumferentially intermediate portions of stent scaffold 100 displaced circumferentially from restraining members 200 are allowed to self-expand. As best seen in FIG. 4, associated portions of stent scaffold 100 constrained by restraining members 200, and portions of the covering 120 attached to those associated portions, remain in their compressed position. Intermediate or leaf portions of the stent scaffold 100 and portions of the covering 120 attached to those intermediate portions expand radially outward against inner surface 2 of body lumen 1.

As sheath 330 is withdrawn distally from the proximal end of endograft 103, the distal end of endograft 103 is still constrained by sheath 330. During this first partially deployed stage, the proximal end of endograft 103 takes on a leaf configuration between the radially constrained portions associated with restraining members 200. A fluid channel 20 remains external to endograft 103 where it is constrained by restraining members 200, while intermediate portions self-expand against inner surface 2 of body lumen 1. While sheath 330 is being withdrawn, there is essentially no flow channel inside of endograft 103, because the distal end of endograft 103 is still constrained by sheath 330. However, flow channel 20, external to endograft 103, prevents pressure build-up on endograft 103 that would otherwise result from the wind sock effect.

Figure 5:
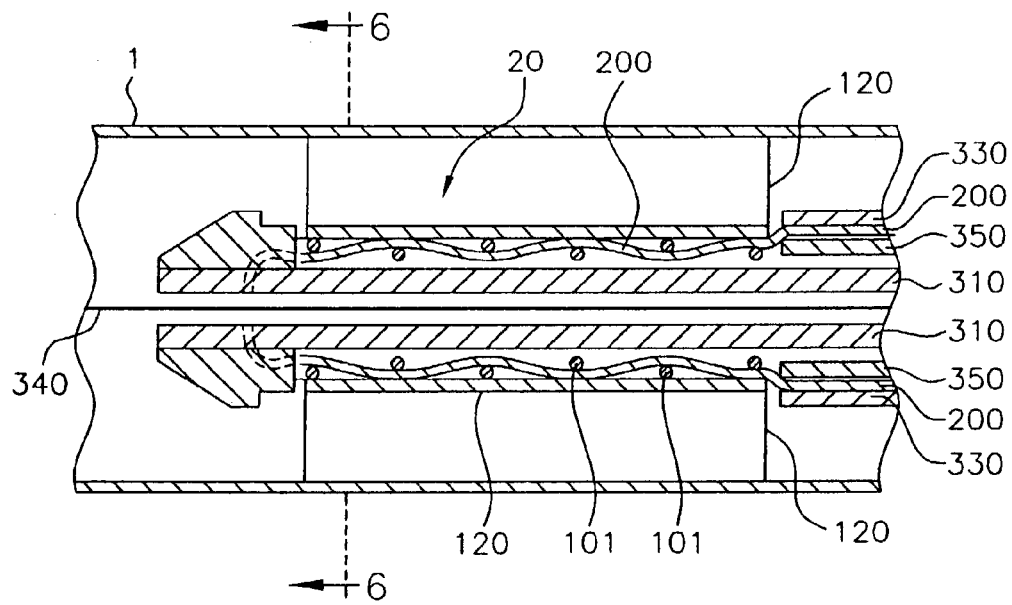
FIG. 5 is a subsequent sequential sectioned side view of the endograft and delivery system of FIGS. 1 and 3 with the endograft at a second partially deployed stage according to an exemplary embodiment of the present invention.

After sheath 330 is fully withdrawn from endograft 103, the endograft expands to a second partially deployed configuration as shown in FIGS. 5 and 6. In this second partially deployed configuration, each of the plurality of restraining members 200 constrain self-expansion of an associated portion of stent scaffold 100 (and a portion of covering 120 attached to such associated portion) along the entire length of endograft 103. Circumferentially intermediate portions of stent scaffold 100 (and portions of covering 120 attached to those intermediate portions) self-expand against inner surface 2 of body lumen 1. In the second partially deployed configuration, fluid channel 20, passing external endograft 103 and within body lumen 1, extends between the intermediate or leaf portions of endograft 103 proximate restraining members 20 along the entire length of endograft 103. Meanwhile, another fluid channel 21 is formed inside of endograft 103 in those leaf portions, when sheath 330 is fully withdrawn from the distal end of endograft 103.

While endograft 103 is in the second partially deployed configuration, as shown in FIGS. 5 and 6, small adjustments may be made to its position. Constraint of associated portions of stent scaffold 100 by restraining members 200 reduces the total outward force exerted by stent scaffold 100. In an exemplary embodiment of the present invention, the position of the partially deployed endograft is determined, such as by radiography. Then, the partially deployed endograft is repositioned as necessary by advancing or withdrawing catheter 310.

After sheath 330 is fully withdrawn from endograft 103 and fluid flow through the partially deployed endograft is established, restraining members 200 are released, allowing endograft 103 to fully deploy. In this fully deployed configuration, shown in FIGS. 7 and 8, the portions of stent scaffold 100 previously constrained by restraining members 200 are allowed to self-expand against inner surface 2 of body lumen 1.

In the fully deployed configuration of endograft 103, as shown in FIGS. 7 and 8, a fluid channel 30 extends through the inside of endograft 103, and covering 120 is pressed against inner surface 2 of body lumen 1 sealing endograft 103 with body lumen 1 and preventing fluid flow between endograft 103 and inner surface 2 of body lumen 1.

Alternatively, restraining members 200 may be released, for example, by severing, absorbing or dissolving restraining member (200 in FIGS. 1–6) or by untying them from a restrained configuration or the like. In one specific alternative embodiment, restraining members 200 comprise stiff elements seated in nosecone 320 and attached to the proximal end of stabilizer 350. Release of these restraining members is achieved by moving nosecone 320 proximally by proximal activation of catheter 310. Upon proximal movement of nosecone 320 a sufficient distance to disengage restraining members 200 from stent members 101, stent scaffold 100 is permitted to expand to its fully expanded configuration. Stabilizer 350 and attached restraining members 200 are then withdrawn, followed by nosecone 320.

In another alternative embodiment, individual members of restraining members 200 may optionally be separately releasable to provide increased control of the self-expansion of stent scaffold 100. This may be particularly advantageous where a larger number of restraining members 200 are provided and it is desirable to release them in a particular sequential order, due to lumen anatomy.

Barbs (not shown) may be provided on stent scaffold 100 for anchoring endograft 103 to lumen wall 1 when associated portions of stent scaffold 100 are released by the restraining members. If the placement of stent barbs is limited to areas adjacent restraining members 200, the barbs may be prevented from contacting inner surface 2 of body lumen 1 while associated portions of the endograft are constrained. The barbs, however, are urged against inner surface 2 of body lumen 1 when restraining members 200 are released. This allows endograft 103 to be securely anchored in the fully deployed configuration, and to be repositioned in the partially deployed configuration.

Figure 9:
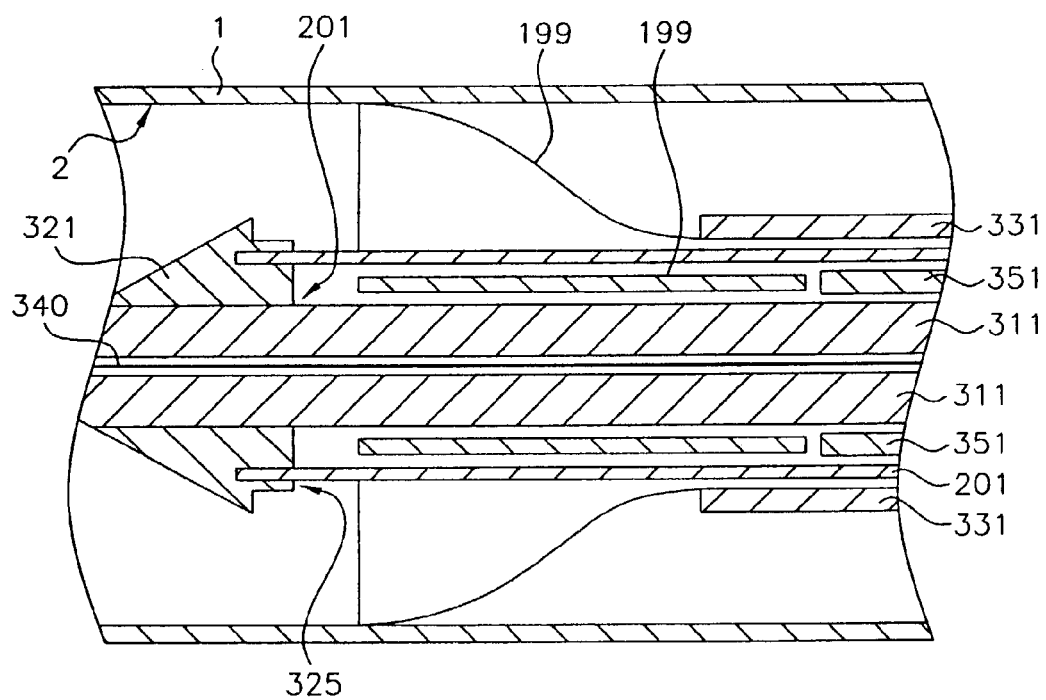
FIG. 9 is a sectioned side view of an endograft and delivery system according to an alternate exemplary embodiment of the present invention.

In an alternative embodiment of the invention as shown in FIG. 9, the restraining members are flexible tubes 201. Flexible tubes 201 are sufficiently flexible to facilitate delivery through tortuous lumen anatomy but still provide some structural stiffness. The stiffness of flexible tubes 201 together with tension applied to flexible tubes 201 from the handle (not shown) may be used to provide the necessary restraining force to constrain associated longitudinal portions of endograft 199. In this configuration, the delivery system is generally similar to the delivery system described above, except as noted below. Flexible tubes 201 extend between stabilizer 351 and sheath 331 over longitudinal portions of an endograft 199 and are seated in apertures 325 in a nosecone 321. Alternatively, flexible tubes 201 may extend between catheter 311 and stabilizer 351, over selected longitudinal portions of endograft 199, and into apertures 325 in nosecone 321. Flexible tubes 201 may be threaded at their distal end and apertures 325 may be threaded to removably receive flexible tubes 201 in threaded engagement.

Endograft 199 may comprise a covered stent scaffold, a balloon-expandable stent-graft, or an unsupported graft. When sheath 331 is withdrawn from endograft 199, flexible tubes 201, supported by nosecone 321 and sheath 331 constrain associated longitudinal portions of endograft 199, preventing them from expanding. Endograft 199 is disposed over catheter 311 and is radially constrained by a sheath 331 during endoluminal delivery. As shown in FIG. 9, in a partially deployed stage corresponding to the first partially deployed stage shown in FIG. 4, as sheath 331 is withdrawn distally over endograft 199, portions of endograft 199 operatively associated with flexible tubes 201 remain in a compressed configuration, while circumferentially intermediate portions of endograft 199 are allowed to expand against inner surface 2 of body lumen 1.

In yet another alternative embodiment (not shown, but similar to the endograft and delivery system in FIG. 9 except as noted below), the restraining members may comprise rod-like elements extending over the endograft and slidably seated in bores formed in the nosecone. During first and second partially deployed stages, these rod-like elements are restrained by the sheath at their distal end and by the walls of the bores in the nosecone at their proximal end. The rod-like elements or tethers attached to the rod-like elements may extend back to the handle for actuation of the rod-like elements. After fluid flow is established within the partially deployed endograft, the rod-like elements are distally actuated to allow expansion of portions of the endograft previously underlying the rod-like elements and fully deploy the endograft.

Thus, the present invention provides an apparatus and method for deploying an endograft in stages such that a fluid channel is maintained throughout deployment.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A tubular endograft adapted to be radially compressed in a first delivery configuration for endoluminal delivery and radially expanded to a second deployment configuration following endoluminal delivery, comprising:

a plurality of longitudinal portions each radially disposed from and substantially parallel to the axis of the tubular endograft and extending along the full length of the endograft, the longitudinal portions collectively forming a common longitudinal lumen therethrough in the expanded configuration; and at least one releasable restraining member operatively associated with a select one of said plurality of longitudinal portions of said endograft, said at least one of releasable restraining member adapted to selectively constrain expansion of the associated longitudinal portion along the full length of said endograft while allowing expansion of unconstrained longitudinal portions of said endograft along the full length thereof.

2. The endograft of claim 1 wherein said at least one restraining member comprises two or more individual restraining members and said individual restraining members are separately releasable.

3. The endograft of claim 1 further comprising a self-expanding stent scaffold and a covering affixed to said stent scaffold;

wherein said restraining member or members is or are entwined in said stent scaffold in the delivery configuration thereof.

4. The endograft of claim 3 wherein said restraining member or members is or are wires.

5. The endograft of claim 3 wherein said restraining member or members is or are sutures.

6. The endograft of claim 3 wherein said at least one restraining member comprises a rod-like element.

7. The endograft of claim 1 wherein said restraining member or members is or are flexible tubes.

8. The endograft of claim 1 further comprising barbs for anchoring said endograft to a body lumen wall.

9. An endograft comprising:
  a self-expanding stent scaffold with a covering affixed thereto said scaffold having at least two portions extending in parallel along the full length of the stent; and
  at least one releasable restraining member disposed lengthwise over an associated portion of said stent scaffold along the full length thereof and adapted to selectively constrain the associated portions from circumferential expansion along the full length thereof;
  the endograft having at least a first configuration in which said endograft is constrained in a circumferentially compressed configuration suitable for endoluminal deployment, a second configuration in which said at least one restraining member selectively constrains the associated portions of said endograft along the full length thereof and non-constrained portions of said endograft are radially expanded forming a fluid passageway therethrough along the full length of said endograft, and a fully deployed configuration in which said endograft is neither circumferentially nor selectively constrained.

10. The endograft of claim 9 wherein two releasable restraining members are disposed at diametrically opposite locations along the length of the endograft.

11. The endograft of claim 9 wherein said stent scaffold is sized and configured to allow said endograft to be repositioned in said second configuration.

12. The endograft of claim 9 wherein said endograft is constrained in said first configuration by a delivery sheath.

13. An endograft comprising:
  a self-expanding stent scaffold with a covering affixed thereto; and
  at least one releasable restraining member disposed lengthwise over an associated portion of said stent scaffold
  the endograft having at least a first configuration in which said endograft is constrained in a compressed configuration suitable for endoluminal deployment, a second configuration in which said at least one restraining member radially constrains the associated portions of said endograft and non-selected portions of said endograft intermediate said associated portions are radially expanded forming a fluid passageway therethrough wherein said endograft provides a fluid channel outside of said covering adjacent said restraining members in said second configuration, and a third configuration in which said at least one restraining member is released and the respective associated portions are radially expanded forming an enlargement of said fluid passageway.

14. The endograft of claim 13 wherein said endograft provides a fluid channel outside of said endograft in said first configuration and during transition from said first configuration to said second configuration; said endograft provides a fluid channel outside and through said endograft in said second configuration; and said endograft provides a fluid channel through said endograft in said third configuration and during transition from said second configuration to said third configuration.

* * * * *